United States Patent [19]

Ozawa et al.

[11] Patent Number: 4,606,854

[45] Date of Patent: Aug. 19, 1986

[54] METHOD OF PREPARING α-L-ASPARTYL-L-PHENYLALANINE METHYL ESTER AND ITS HYDROCHLORIDE

[75] Inventors: Yoichi Ozawa, Yokohama; Shinichi Kishimoto, Yokkaichi; Emiko Shinohara, Saga; Tadashi Takemoto, Kawasaki; Chikahiko Eguchi, Yokohama, all of Japan

[73] Assignee: Ajinomoto Co., Inc., Tokyo, Japan

[21] Appl. No.: 611,531

[22] Filed: May 17, 1984

[30] Foreign Application Priority Data

May 28, 1983 [JP] Japan .................. 58-94477

[51] Int. Cl.⁴ ............................. C07K 5/06
[52] U.S. Cl. ....................................... 560/19
[58] Field of Search .................. 260/112.5 R

[56] References Cited

U.S. PATENT DOCUMENTS

| | | | |
|---|---|---|---|
| 3,798,207 | 3/1974 | Ariyoshi et al. | 260/112.5 R |
| 4,111,925 | 9/1978 | Bachman | 260/112.5 R |
| 4,173,562 | 11/1979 | Bachmann et al. | 260/112.5 R |

FOREIGN PATENT DOCUMENTS 0127411 5/1984 European Pat. Off. .

OTHER PUBLICATIONS

Solomons, *Organic Chemistry*, John Wiley and Sons, N.Y., 1978, pp. 756-759.
Battershy et al., *J. Chem. Soc.*, 1955, 259-269.
Chemical Abstracts, vol. 99, No. 1, Jul. 4th, 1983, Columbus, Ohio, USA; p. 412, column 1, Abstract No. 4364p & CS-A-210 016 (F. Jancik et al.) 15-07-1982 (Cat. A).

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

A method for preparing α-L-aspartyl-L-phenylalanine methyl ester and its hydrochloride which comprises dissolving α-L-aspartyl-L-phenylalanine dimethyl ester in a mixture of 0–10% (v/v) methanol, 8–55% (v/v) of concentrated hydrochloric acid, and water (remainder) to a concentration of 0.01 mol/dl to 0.30 mol/dl; holding the resulting solution at one or more temperatures between 0° and 60° C. for a time sufficient for crystals of α-L-aspartyl-L-phenylalanine methyl ester hydrochloride to precipitate out, and isolating the crystals. The hydrochloride may then be treated with alkali to yield α-L-aspartyl-L-phenylalanine methyl ester.

5 Claims, No Drawings

METHOD OF PREPARING α-L-ASPARTYL-L-PHENYLALANINE METHYL ESTER AND ITS HYDROCHLORIDE

DETAILED DESCRIPTION OF THE INVENTION

This invention relates to a method of preparing α-L-aspartyl-L-phenylalanine methyl ester (hereinafter abbreviated as "α-APM"), which is a peptide sweetener of commercial value, and its hydrochloride.

Various methods are known for the manufacture of α-APM.

In accordance with most of these methods, L-aspartic acid (hereinafter abbreviated as "L-Asp"), after its amino group has previously been protected by some means, for example, with a carbobenzoxy group, a formyl group, a hydrogen halide or other protective groups, is converted to its anhydride, and then the anhydride is condensed with L-phenylalanine methyl ester (hereinafter abbreviated as "PM") to form the skeleton of α-APM, followed by removal of the protective group. One of the disadvantages of these methods is a certain limitation of the yield of α-APM obtainable because of the formation of the by-product β-L-aspartyl-L-phenylalanine methyl ester (hereinafter abbreviated as "β-APM") which is unavoidable in the synthesis of α-APM from L-Asp or L-phenylalanine (hereinafter abbreviated as "L-Phe"). Furthermore, an additional step for isolating α-APM from the α- and β-APM isomeric mixture is required.

On the other hand, several methods have been proposed for chemical synthesis of pure α-APM alone. For example, a Japanese Patent Application No. (tokkaisho 56-73053) teaches a method in which an N-thiocarboxy anhydride of L-Asp is condensed with PM. However, this method also has disadvantages such as disagreeable smell of the final product, and, therefore, is not suitable for commercial production. Another Japanese Patent Application No. (tokkaisho 48-96557) discloses a method which comprises condensing the N-carboxy anhydride (NCA) derived from N-carbobenzoxy-L-aspartic acid β-benzyl ester with PM, followed by removal of the protective group through catalytic reduction to obtain α-APM. However, its commercial application also seems to be difficult because of high cost among other reasons. Several other methods are also known for the manufacture of α-APM without forming β-APM as a by-product. Although practical in laboratories, all of these methods have little feasibility on a commercial basis in terms of cost, availability of auxiliary materials and other factors.

The present inventors have discovered that α-APM can be easily prepared in high yields using α-L-aspartyl-L-phenylalanine dimethyl ester [$CH_3O-COCH_2CH(NH_2)CONHCH(CH_2C_6H_5)COOCH_3$; hereinafter abbreviated as "α-APM$_2$"] as the starting material.

The present inventors previously found that, when α-APM is allowed to stand in a mixed solvent of methanol (hereinafter abbreviated as "MeOH") and hydrochloric acid, α-APM hydrochloride crystallizes out from the solution and, at the same time, α-APM$_2$ is formed in the mother liquor. It was inferred that α-APM$_2$ is formed through esterification of the β-carboxyl group of the L-Asp residue in α-APM. Incidentally, it was also inferred that an equilibrium is established among the compounds contained in the system.

The present inventors' further studies have revealed that α-APM$_2$ undergoes hydrolysis to form α-APM followed by crystallization of its hydrochloride, if α-APM$_2$ is allowed to stand under specific conditions that favor hydrolysis. That is, by dissolving -AMP$_2$ in a mixed solvent of MeOH and hydrochloric acid consisting of 0 to 10% by volume of MeOH, 8 to 55% by volume of concentrated hydrochloric acid and water (balance), the hydrochloric acid being expressed as a mixture of concentrated hydrochloric acid and water, in a concentration ranging from 0.01 mol/dl to 0.3 mol/dl, and holding the solution at temperatures between 0° and 60° C., during which holding the temperature may be kept constant or may fluctuate within this range, whereby the α-APM$_2$ is converted into α-APM by hydrolysis and the α-APM is crystallized as its hydrochloride in a high yield (about 70% or higher on the basis of the starting α-APM$_2$). This invention has been accomplished based on these findings. Incidentally, it is known that α-APM hydrochloride is very sparingly soluble (U.S. Pat. No. 3,798,207).

Synthesis of α-APM through ester hydrolysis as described above has not been reported yet. If MeOH is used in larger amounts, no hydrolysis of ester takes place, while an insufficient amount of MeOH causes hydrolysis to proceed too extensively. If concentrated hydrochloric acid is used in excess of the amount required to ensure crystallization of α-APM hydrochloride, this means waste of the acid, while an insufficient amount results in lower rate of hydrolysis and difficulty in crystallization of the α-APM hydrochloride. A higher reaction temperature leads to fission of the peptide linkage, while lower temperature slows down ester hydrolysis.

If MeOH, concentrated hydrochloric acid or hydrochloric acid of appropriate concentration, and water are added to the mother liquor from which the crystals of α-APM hydrochloride have been separated so as to satisfy the above-mentioned conditions, followed by addition of α-APM$_2$, substantially all the α-APM$_2$ used as the starting material can be quantitatively converted to α-APM hydrochloride without any loss. When the composition of the mother liquor comes out of the above-specified conditions as a result of crystallization of α-APM hydrochloride, an additional amount of the hydrochloride may be crystallized by adding MeOH, hydrochloric acid and α-APM$_2$, without separating the crystals of α-APM hydrochloride formed, so as to adjust the liquor composition.

Crystals of α-APM can be obtained by neutralizing the α-APM hydrochloride with a suitable alkali such as sodium carbonate.

α-APM can thus be easily synthesized from α-APM$_2$ according to the process described above.

α-APM$_2$ used as the starting material in the process of this invention can be readily obtained, for example, by the following methods: Condensation of the NCA of L-Asp β-methyl ester with PM in an organic solvent or a mixture of an organic solvent and water; condensation of N-formylaspartic acid anhydride with PM, followed by treatment with an anhydrous methanol solution of hydrogen chloride to effect removal of the formyl group and esterification; treatment of N-formylaspartyl-phenylalanine with an anhydrous methanol solution of hydrogen chloride to effect removal of the formyl group and di-esterification; treatment of N-formylaspartylphenylalanine methyl ester with an anhydrous methanol solution of hydrogen chloride to effect removal of the formyl group and esterification of the β-carboxyl group of the Asp residue in the starting N-formylaspartylphenylalanine methyl ester; and treatment of aspartylphenylalanine produced, for example, by a biotechnological method with an anhydrous methanol solution of hydrogen chloride to effect di-esterification.

This invention will be explained in more detail by the examples that follow.

Preparation of α-APM$_2$

A 1 liter toluene solution containing 1 mol (179 g) PM was cooled to −30° C. To the cooled solution was added a 500 ml toluene solution cooled to 0° C. and containing 0.5 mol (73 g) of the NCA of L-Asp β-methyl ester with vigorous stirring over a period of 15 minutes. Stirring was continued for further 30 minutes. Then, the reaction mixture was concentrated under reduced pressure below 50° C.

It was found by the HPLC analysis that the resulting oily residue contained 0.32 mol of the desired substance. Yield, 64%.

Preparation of α-APM$_2$.HCl

To a 200 ml toluene solution containing 17.9 g PM was added a 100 ml toluene slurry containing 14.3 g N-formyl-L-aspartic acid anhydride, and the mixture was stirred at room temperature for three hours.

The reaction product was concentrated under reduced pressure, 1 liter of anhydrous methanol containing hydrogen chloride (13%) was added to the concentrate, and the mixture was allowed to stand overnight and concentrated, whereby 35 g of α-APM$_2$ hydrochloride (syrup) was obtained.

EXAMPLE 1

Hydrochloride of α-L-aspartyl-L-phenylalanine dimethyl ester (α-APM$_2$.HCl) (51.6 g, 0.15 mol) was dissolved in a mixed solvent consisting of 3.5 ml MeOH, 42 ml concentrated hydrochloric acid and 25 ml water, and the solution was held at 25° C.

Hydrolysis of the ester gradually proceeded with the passage of time, while the α-APM thus formed was crystallized as its hydrochloride. The crystals collected after four days gave 69.6% yield, and after seven days, 81% yield (40.2 g).

EXAMPLE 2

α-APM$_2$ hydrochloride (51.6 g, 0.15 mol) was dissolved in a mixed solvent consisting of 42 ml concentrated hydrochloric acid and 29 ml water, and the solution was held at 25° C.

After eight days, α-APM hydrochloride was collected by filtration with 69.6% yield.

EXAMPLE 3

α-APM$_2$ hydrochloride (51.6 g, 0.15 mol) was dissolved in a mixed solvent consisting of 4 ml MeOH, 42 ml concentrated hydrochloric acid and 25 ml water, and the solution was held at 35° C. for one day and at 25° C. for an additional five days.

The yield of α-APM hydrochloride collected by filtration was 80% (39.5 g).

EXAMPLE 4

4 g α-APM hydrochloride was dissolved in 100 ml water and the resultant solution was, while maintained at a lowered temperature, while the pH was adjusted to 4.8 with an aqueous Na$_2$CO$_3$-saturated solution. The resultant neutralized solution was kept at 5° C. overnight.

The crystals precipitated were collected by filtering and dried to give 2.65 g α-APM.

What is claimed as new and desired to be secured by Letters Patent of the United States is:

1. A method for preparing α-L-aspartyl-L-phenylalanine methyl ester hydrochloride which comprises:
   dissolving α-L-aspartyl-L-phenylalanine dimethyl ester in a mixture of water, methanol and hydrochloric acid, said mixture containing from about 0 to 10% by volume of methanol, from about 8 to 55% by volume of concentrated hydrochloric acid and the remainder being water, the concentration of said dimethyl ester in said mixture being from about 0.01 mol/dl to 0.3 mol/dl, thereby yielding a solution;
   holding said solution at one or more temperatures of from about 0° C. to 60° C., until α-L-aspartyl-L-phenylalanine methyl ester hydrochloride crystallizes from said solution; and
   isolating said α-L-aspartyl-L-phenylalanine methyl ester hydrochloride.

2. A method for preparing α-L-aspartyl-L-phenylalanine methyl ester which comprises:
   dissolving α-L-aspartyl-L-phenylalanine dimethyl ester in a mixture of water, methanol and hydrochloric acid, said mixture containing from about 0 to 10% by volume of methanol, from about 8 to 55% by volume of concentrated hydrochloric acid and the remainder being water, the concentration of said dimethyl ester in said mixture being from about 0.01 mol/dl to 0.3 mol/dl, thereby yielding a solution;
   holding said solution at one or more temperatures of from about 0° C. to 60° C. until α-L-aspartyl-L-phenylalanine methyl ester hydrochloride crystallizes from said solution;
   neutralizing said hydrochloride with a base; and
   isolating said α-L-aspartyl-L-phenylalanine methyl ester.

3. The method of claim 1 wherein said holding step is conducted at approximately one temperature.

4. The method of claim 2 wherein said holding step is conducted at approximately one temperature.

5. The method of claim 2 wherein the base is sodium carbonate.

* * * * *